(12) United States Patent
Lessne

(10) Patent No.: US 9,427,287 B2
(45) Date of Patent: Aug. 30, 2016

(54) MULTI-COMPARTMENT INTERVENTIONAL WIRE AND CATHETER STORAGE SYSTEMS

(71) Applicant: Duke University, Durham, NC (US)

(72) Inventor: Mark L. Lessne, Durham, NC (US)

(73) Assignee: Duke University, Durham, NC (US)

( * ) Notice: Subject to any disclaimer, the term of this patent is extended or adjusted under 35 U.S.C. 154(b) by 29 days.

(21) Appl. No.: 14/315,276

(22) Filed: Jun. 25, 2014

(65) Prior Publication Data
US 2014/0374295 A1 Dec. 25, 2014

Related U.S. Application Data

(60) Provisional application No. 61/839,050, filed on Jun. 25, 2013.

(51) Int. Cl.
| | |
|---|---|
| *B65D 83/10* | (2006.01) |
| *A61B 19/02* | (2006.01) |
| *A61M 25/00* | (2006.01) |
| *B65D 85/671* | (2006.01) |

(52) U.S. Cl.
CPC ............ *A61B 19/026* (2013.01); *A61B 50/20* (2016.02); *A61B 50/30* (2016.02); *A61M 25/002* (2013.01); *B65D 85/671* (2013.01); *A61B 2050/3006* (2016.02)

(58) Field of Classification Search
CPC .......... B65D 7/46; B65D 7/44; B65D 11/24; B65D 11/22; B65D 83/10; B65D 21/0233; B65D 85/671; A61M 25/00; A61M 25/002; A61B 19/02; A61B 2019/0209; A61B 2019/0278; A61B 19/026; A61B 50/20; A61B 50/30

USPC ....... 206/364, 366, 370, 372, 380, 557, 485, 206/494, 574, 314, 316, 438, 303, 499–502, 206/503, 505, 507, 509, 564; 220/669–671, 220/673, 675, 676, 574.3; 242/602, 602.1, 242/602.2, 602.3, 588
See application file for complete search history.

(56) References Cited

U.S. PATENT DOCUMENTS

| | | | | |
|---|---|---|---|---|
| 4,936,448 A | | 6/1990 | Holloway | |
| 5,564,589 A | * | 10/1996 | Fu | A47J 27/002 220/573.1 |
| 5,738,213 A | * | 4/1998 | Whiting | A61M 25/002 206/210 |
| 8,701,549 B2 | * | 4/2014 | Mordini | A47J 31/0615 99/304 |
| 2006/0260968 A1 | * | 11/2006 | Mayda | A61M 25/002 206/438 |

* cited by examiner

*Primary Examiner* — Jacob K Ackun
*Assistant Examiner* — Rafael Ortiz
(74) *Attorney, Agent, or Firm* — Olive Law Group, PLLC

(57) ABSTRACT

Multi-compartment interventional wire and catheter storage systems are disclosed. According to an aspect, a storage system includes a bottom wall and a side wall. The side wall includes an upper end and an opposing lower end attached to the bottom wall. The side wall defines multiple interior passageways between the upper and lower ends. Further, the side wall defines multiple openings at the upper end. Each opening extends to a respective one of the interior passageways for storage of elongated flexible members, such as catheters and guide wires.

14 Claims, 10 Drawing Sheets

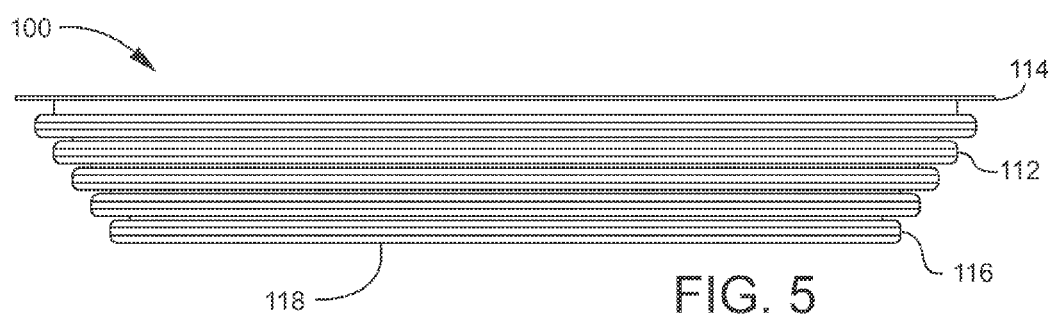
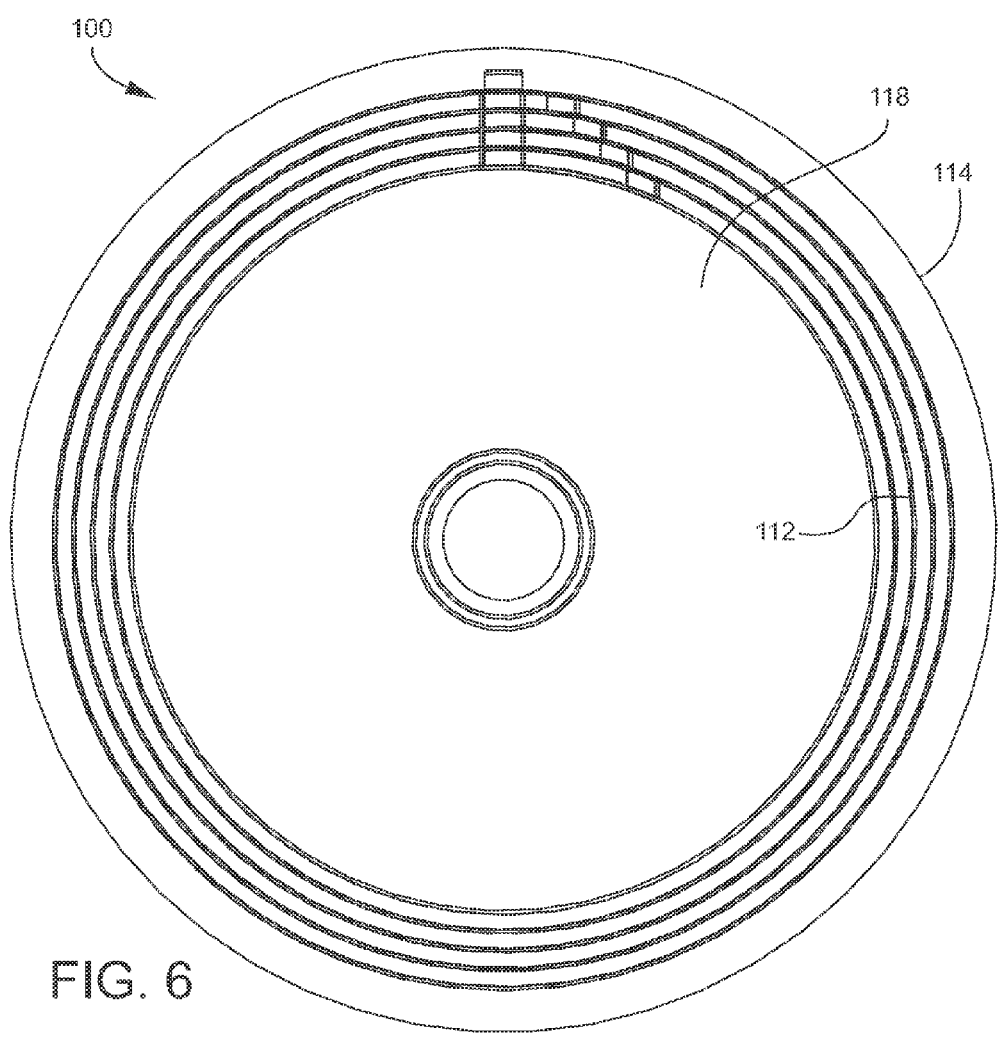

US 9,427,287 B2

MULTI-COMPARTMENT INTERVENTIONAL WIRE AND CATHETER STORAGE SYSTEMS

CROSS REFERENCE TO RELATED APPLICATION

This application claims the benefit of and priority to U.S. Provisional Patent Application No. 61/839,050, filed Jun. 25, 2013 and titled MULTICOMPARTMENT INTERVENTIONAL WIRE AND CATHETER STORAGE SYSTEM; the disclosure of which is incorporated herein by reference in its entirety.

TECHNICAL FIELD

The presently disclosed subject matter relates to medical equipment storage. Particularly, the presently disclosed subject matter relates to multi-compartment interventional wire and catheter storage systems.

BACKGROUND

The ubiquitous utilization of wires for catheter directed therapy has revolutionized medical care in the fields of interventional radiology, neuroradiology, cardiology, and neurosurgery, among others. However, since the initial advent of wire and catheter directed therapeutics, more complex techniques have been developed that required complimentary development of equally advanced and expensive wires and catheters. Often, the more sophisticated interventions may require multiple wires, catheters, and microcatheters to complete the procedure. These lengthy wires and catheters are often difficult to store and control outside the body, and current storage systems are suboptimal for rapid storage and retrieval of the individual desired wire or device; moreover, a single unintentionally dropped or contaminated wire or catheter can equate to a substantial financial loss in the order of hundreds of dollars.

Currently, the most common technique to store wires uses a single sterile plastic basin containing saline fluid in which all wires used during the procedure are stored. Small caliber, long wires are difficult to find and differentiate from each other, often tangle with other wires, and commonly snag the other stored wires during retrieval from the basin, unintentionally pulling them to the floor or allowing for contamination. Therefore, there is a need for improved storage and retrieval systems for wires and catheters used in the medical setting.

BRIEF SUMMARY

Disclosed herein are multi-compartment interventional wire and catheter storage systems. According to an aspect, a storage system includes a bottom wall and a side wall. The side wall includes an upper end and an opposing lower end attached to the bottom wall. The side wall defines multiple interior passageways between the upper and lower ends. Further, the side wall defines multiple openings at the upper end. Each opening extends to a respective one of the interior passageways for storage of elongated flexible members, such as catheters and guide wires.

BRIEF DESCRIPTION OF THE SEVERAL VIEWS OF THE DRAWINGS

The foregoing aspects and other features of the present subject matter are explained in the following description, taken in connection with the accompanying drawings, wherein:

FIG. 5 is a side view of the system shown in FIG. 1;

FIG. 6 is a top view of the system shown in FIG. 1;

DETAILED DESCRIPTION

For the purposes of promoting an understanding of the principles of the present disclosure, reference will now be made to various embodiments and specific language will be used to describe the same. It will nevertheless be understood that no limitation of the scope of the disclosure is thereby intended, such alteration and further modifications of the disclosure as illustrated herein, being contemplated as would normally occur to one skilled in the art to which the disclosure relates.

The present disclosure provides multi-compartment interventional wire and catheter storage systems. The systems described herein can allow for the separate, compartmentalized storage of wires and catheters, facilitating easy recognition and retrieval of a specific desired wire or catheter. The system may be made of any suitable non-reusable, sterile material as will be appreciated by those of skill in the art. The wires may be hydrophilic wires stored in saline solution the system to maintain a suitable level of hydration, while avoiding tangles, snags, and contamination.

Figure 1:
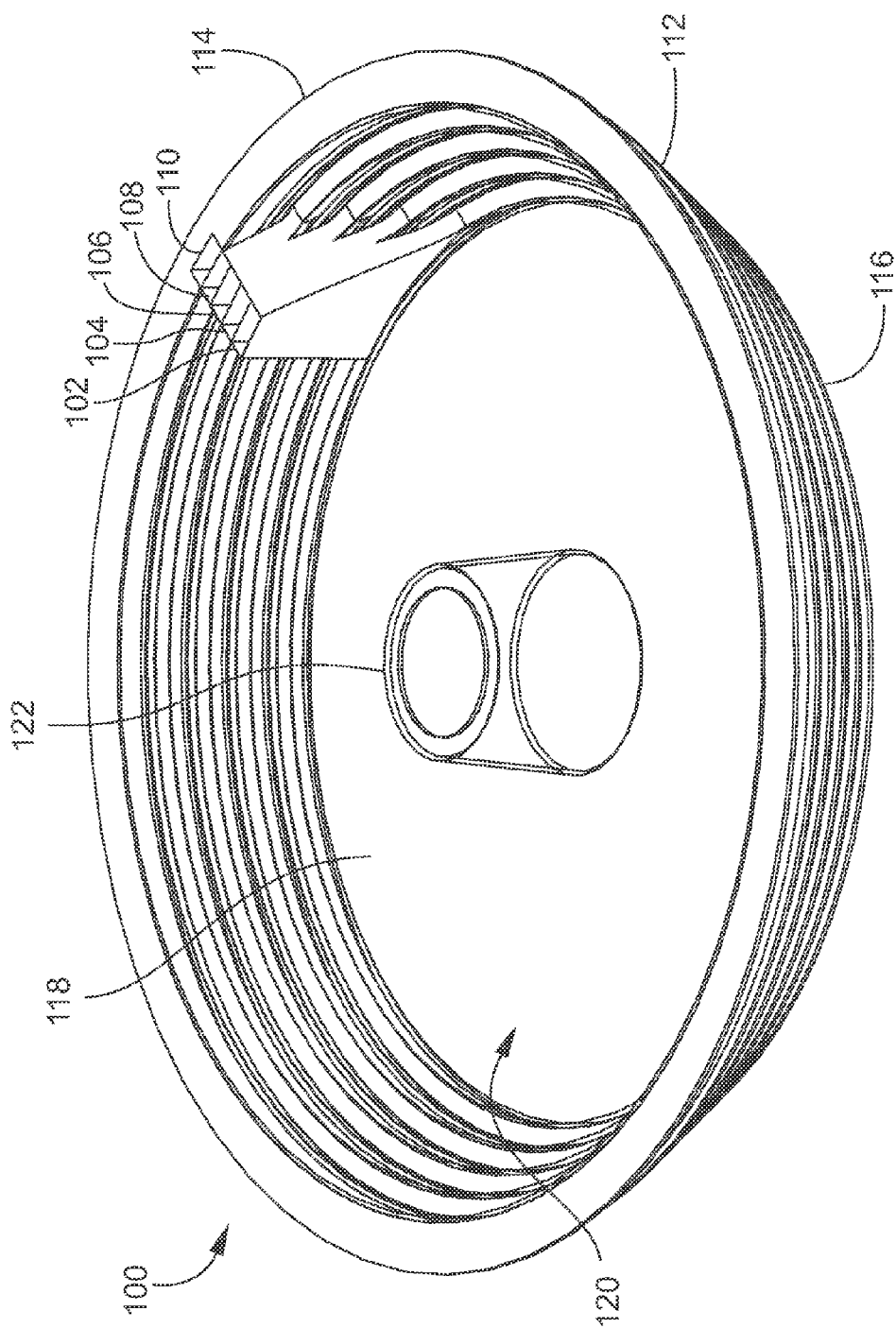
FIG. 1 is a top perspective view of a multi-compartment interventional wire and catheter storage system in accordance with embodiments of the present disclosure.

FIG. 1 illustrates a top perspective view of a multi-compartment interventional wire and catheter storage system 100 in accordance with embodiments of the present disclosure. The system 100 may be used to store multiple interventional wires and/or catheters. Alternatively, the system 100 may be used to store any other suitable types of flexible elongated members. During storage, ends of the wires or catheters may extend from the openings 102, 104, 106, 108, and 110 for retrieval. For example, a healthcare professional may grasp an end of a wire and pull to remove the remainder of the wire from storage within the system 100 for use in a medical procedure. The wire or catheter portion not extending through one of the openings may reside within an interior passageway of a side wall 112 of the system 100 as described in further detail herein.

The side wall 112 may include an upper end 114 and an opposing lower end 116 attached to a bottom wall 118. As shown, the side wall 112 and bottom wall 118 form a bowl shape. The side wall 112 is a continuous side wall that surrounds the bottom wall 118. The side wall 112 and bottom wall 118 may be sealably attached together for retaining saline solution or other liquid within an interior space 120 formed by the side wall 112 and the bottom wall 118.

Figure 2:
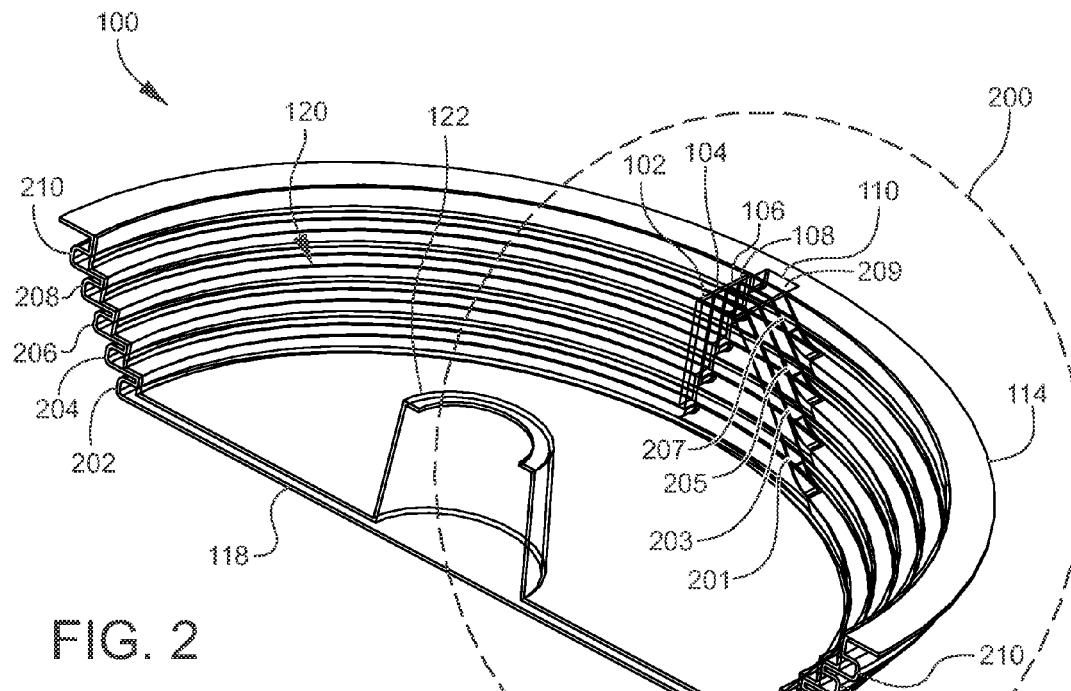
FIG. 2 is a vertical cross-sectional, perspective view of the system shown in FIG. 1.
Figure 3:
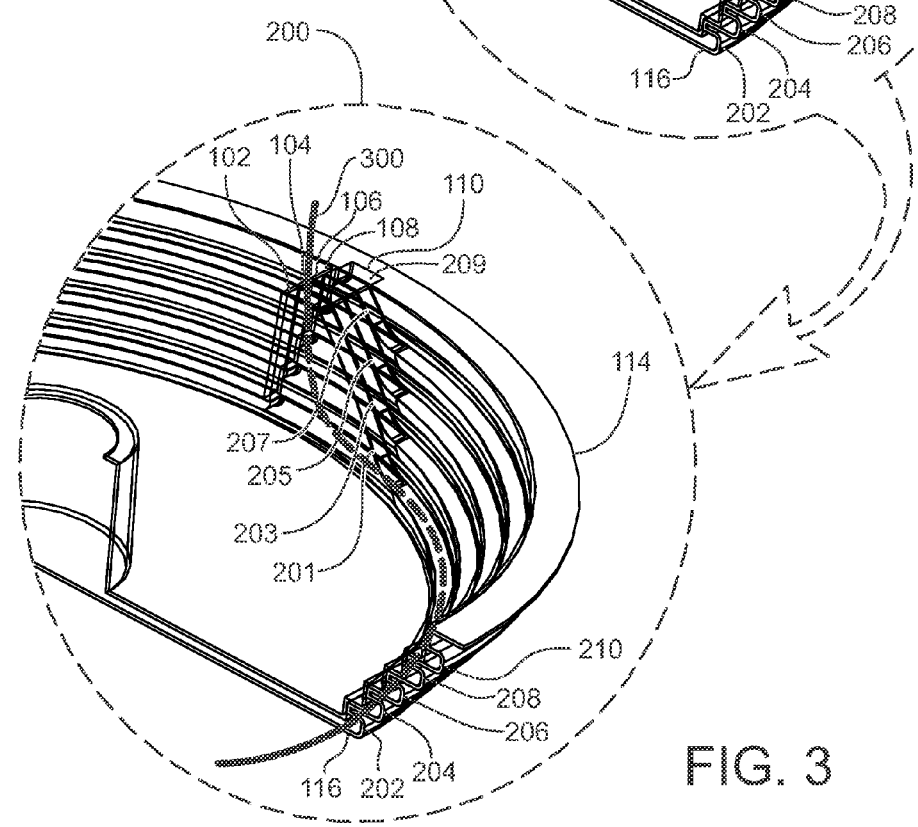
FIG. 3 is a partial, vertical cross-sectional view of a semi-transparent portion of the system shown in FIG. 2.

Now referring to FIG. 2, this figure illustrates a vertical cross-sectional, perspective view of the system 100 shown in FIG. 1. The cross-section shown in the figure is in a vertical direction across the center of the system 100. A portion (depicted within circle 200) of the system 100 shown in FIG. 1 is depicted as being semi-transparent. FIG. 3 shows additional details of this semi-transparent portion. As shown in FIG. 2, the side wall 112 defines interior passageways 202, 204, 206, 208, and 210 positioned between the upper end 114 and lower end 116. Each passageway 202, 204, 206, 208, and 210 is curved in shape and extends in a loop shape within the interior of the side wall 112. The passageways 202, 204, 206, 208, and 210 are positioned at different distances between the upper end 114 and the lower end 116. A passageway may hold one or more guide wires or catheters. Although in this example the interior passageways are shown in a particular orientation and extending in a complete loop within the sidewall, it should be understood that passageways within the sidewall may have any other suitable orientation, shape, or size.

With continuing reference to FIGS. 2 and 3, each opening 102, 104, 106, 108, and 110 defines pathways 201, 203, 205, 207, and 209, respectively, to connect the openings to interior passageways 202, 204, 206, 208, and 210, respectively. For example, opening 102 and interior passageway 202 are connected by pathway 202 such that a wire 300 can be coiled within the interior passageway 202 with its end extending out of the opening 102 to the exterior as shown in FIG. 3. From this configuration, the exposed end of the wire 300 may be pulled to retrieve the remainder of the wire from storage in the system 100. Wires or catheters stored in the passageways 202, 204, 206, 208, and 210 may be similarly stored and retrieved. The pathways 201, 203, 205, 207, and 209 and passageways 202, 204, 206, 208, and 210 may function as compartments for storage of wires, catheters, or other flexible elongated members.

Each pathway 201, 203, 205, 207, and 209 tapers from an end connecting to its respective interior passageway to an opposing end at its respective opening. In this example, the pathways are each triangular in shape. It should be understood that the pathways may alternatively be any other suitable shape and size.

Now referring to FIGS. 1-3, the system 100 may include a protruding structure 122 that extends upwards from the bottom wall 118. The structure 122 may be positioned within the interior space 120 defined by the side wall 112. In this example, the structure is conical in shape and positioned in the center of the interior space 120. It should be understood that in the alternative, the structure 122 may be any other shape or size, and positioned elsewhere. The structure 122 may be used for wrapping wires or catheters. In another use, the structure 122 may be used to lock to a lid or covering for the system 100. The lid or covering may prevent contaminants from entering the system.

Figure 4:
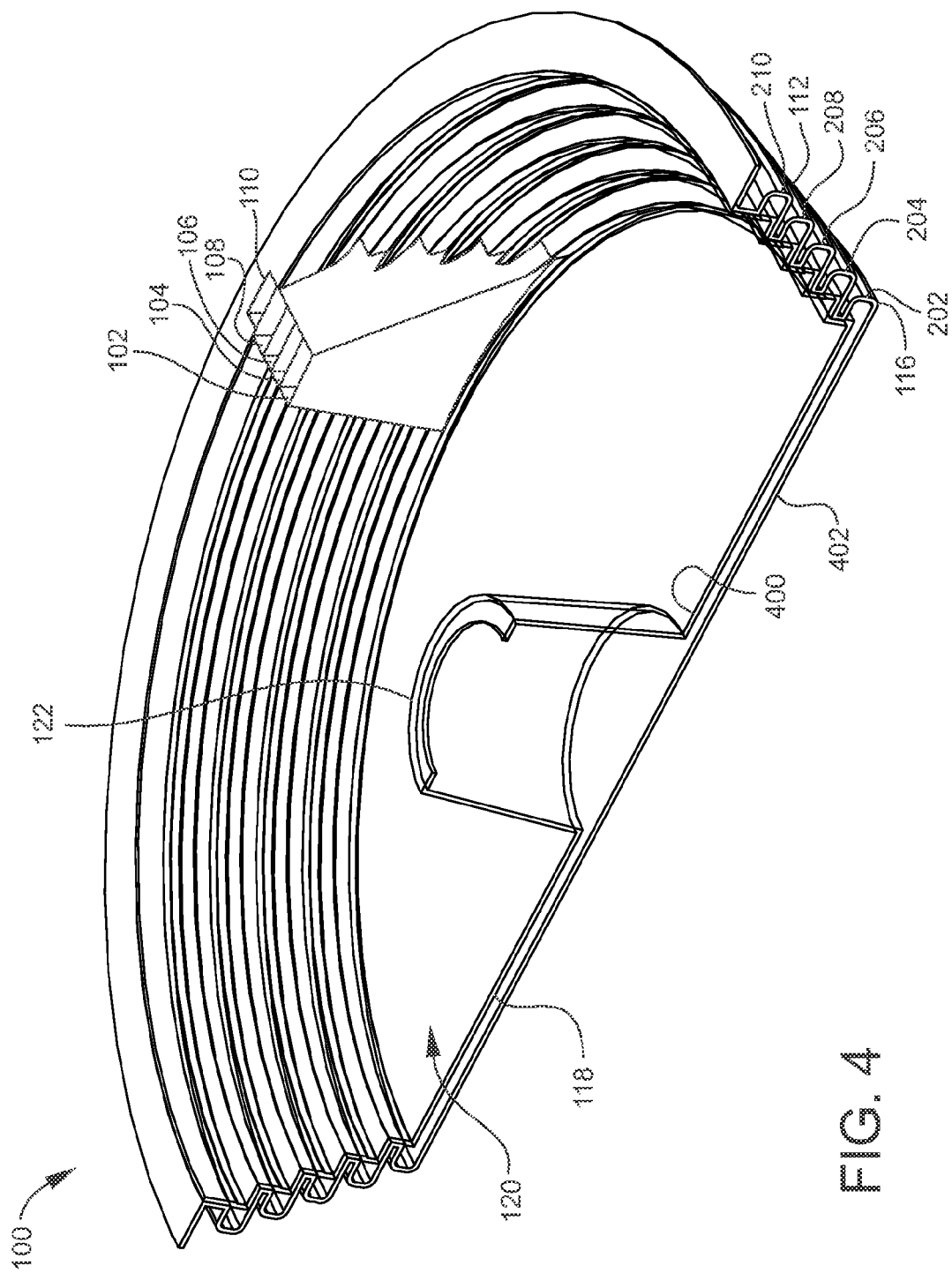
FIG. 4 is another vertical cross-sectional, perspective view of the system shown in FIG. 1.

FIG. 4 illustrates another vertical cross-sectional, perspective view of the system 100 shown in FIG. 1. In this figure, the portion 200 shown in FIGS. 2 and 3 is not transparent. Referring to FIG. 4, it is shown that the side wall 112 and the bottom wall 118 are formed by an interior component 400 and an exterior component 402. The components 400 and 402 have facing surfaces that attach together to form the interior passageways 202, 204, 206, 208, and 210. Attachment of the components 400 and 402 may also form the pathways 201, 203, 205, 207, and 209 shown in FIGS. 2 and 3. The components 400 and 402 may be suitably attach such as by one or more snap lock features or an adhesive.

Figure 7:
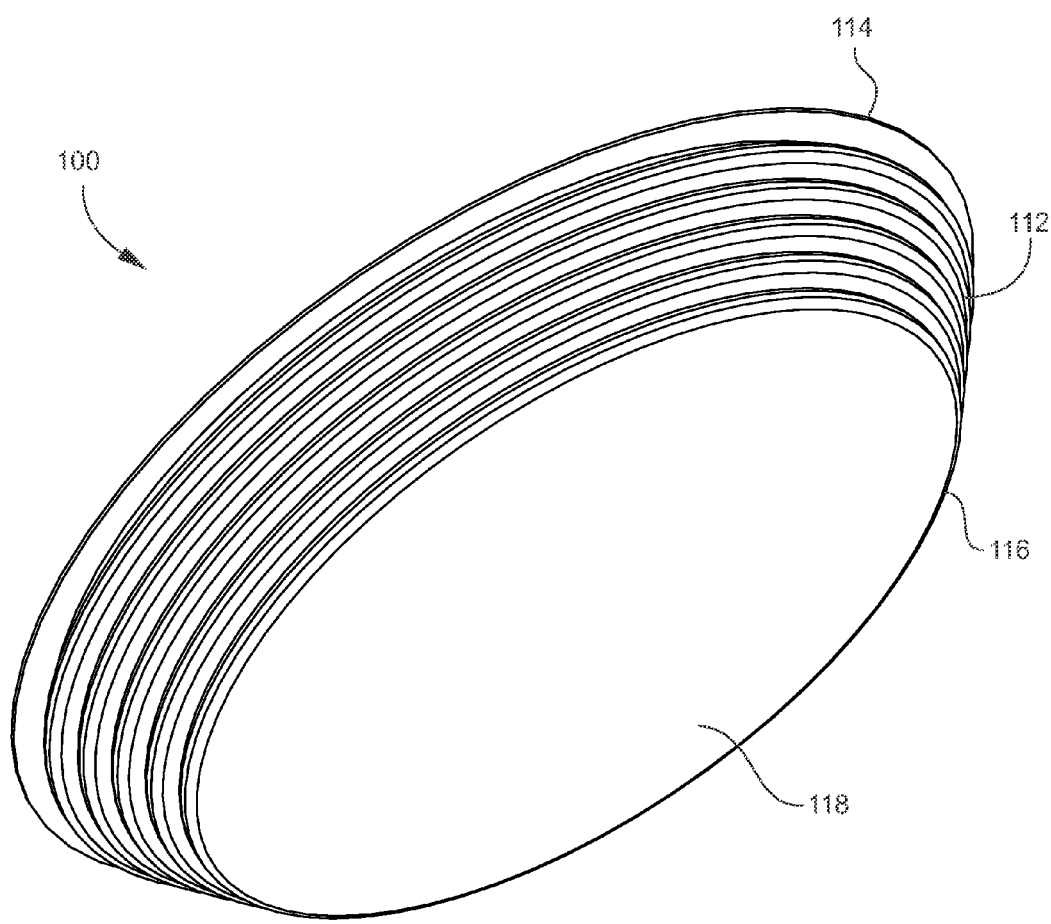
FIG. 7 is a bottom perspective view of the system shown in FIG. 1.

FIGS. 5-7 illustrate other views of the system 100 shown in FIG. 1. Particularly, FIG. 5 illustrates a side view of the system 100, FIG. 6 illustrates a top view of the system 100, and FIG. 7 illustrates a bottom perspective view of the system 100.

Figure 8:
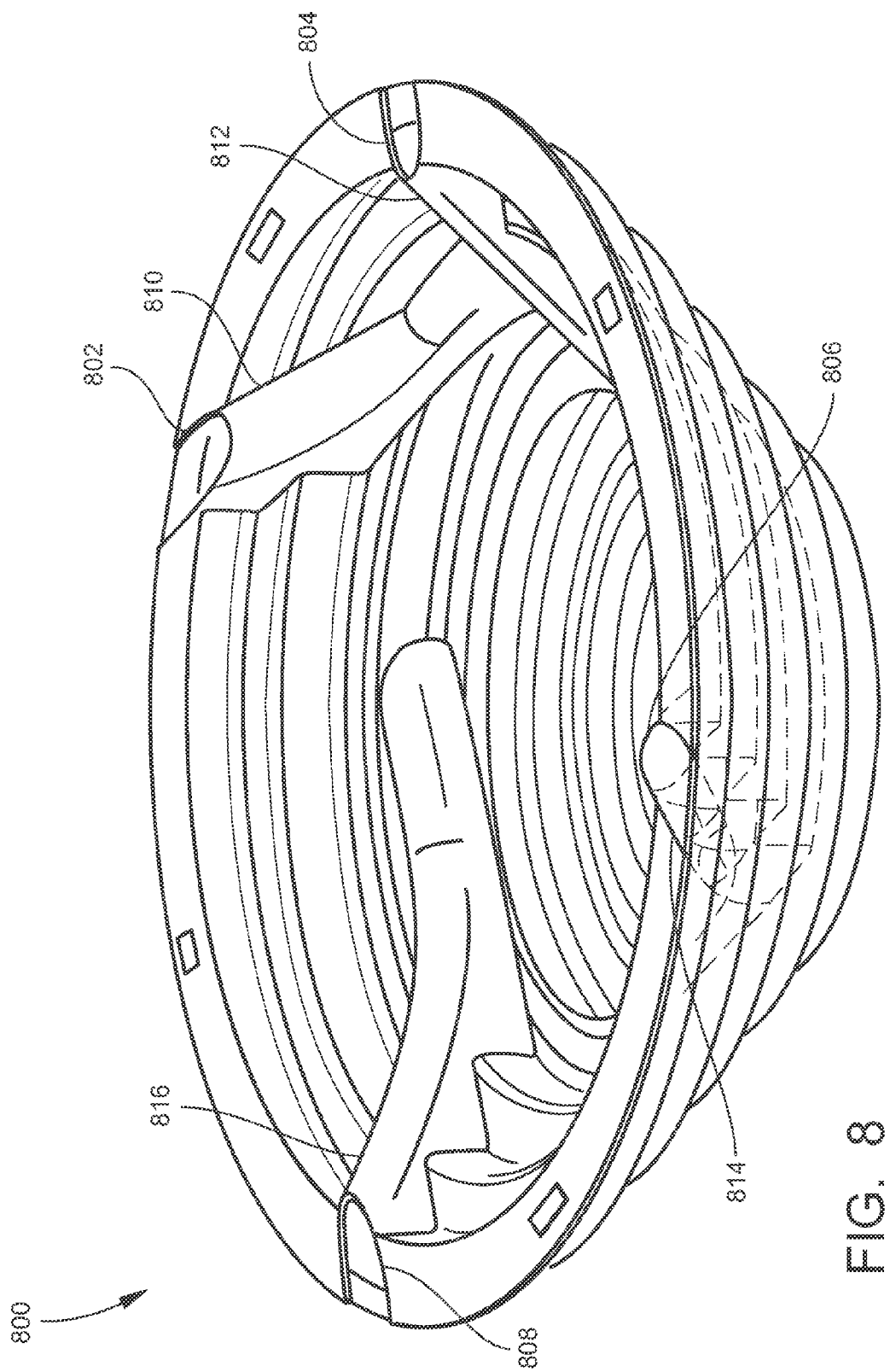
FIG. 8 is a top perspective view of another storage system in accordance with embodiments of the present disclosure.
Figure 9:
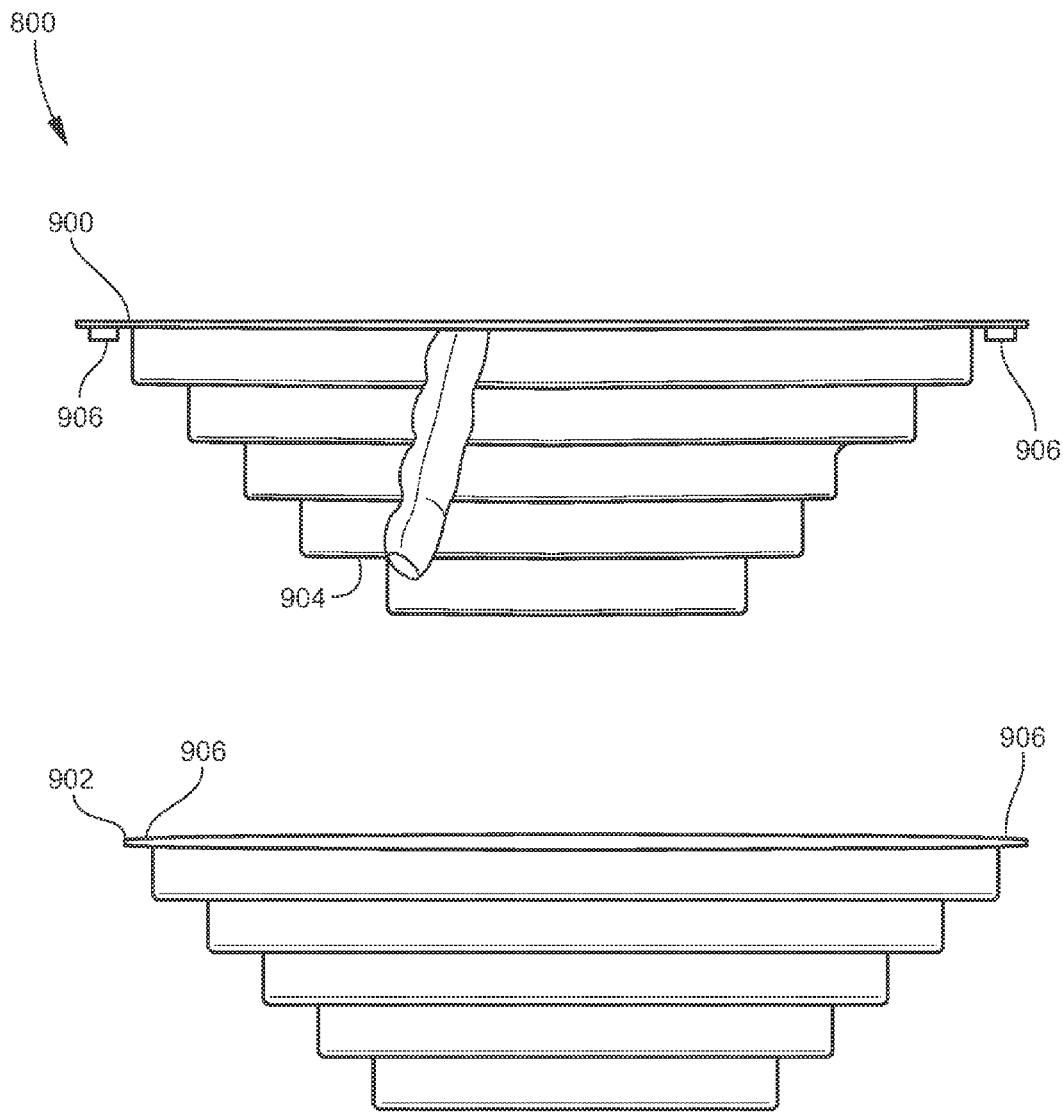
FIG. 9 is an exploded side view of the system shown in FIG. 8.
Figure 10:
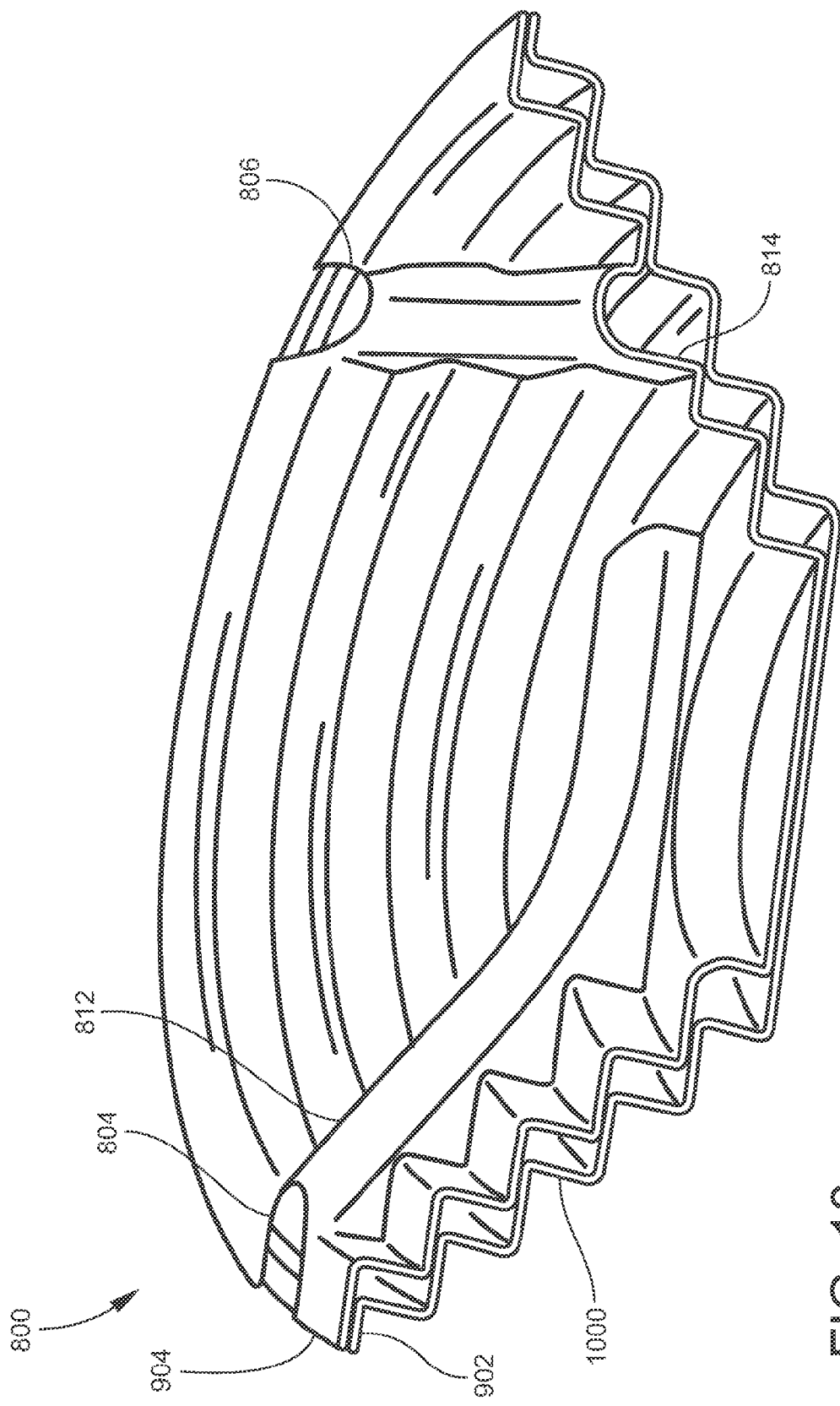
FIG. 10 is a side view of the system shown in FIG. 8.

FIGS. 8-10 illustrate different views of another multi-compartment interventional wire and catheter storage system 800 in accordance with embodiments of the present disclosure. Storage system 800 has openings, pathways, and passageways similar to the system 100 shown in FIGS. 1-7. Referring to FIG. 8, the figure shows a top perspective view of the storage system 800 having multiple openings 802, 804, 806, and 808 that define pathways 810, 812, 814, and 816, respectively. The pathways 810, 812, 814, and 816 connect to pathways similar to the system 100 shown in FIGS. 1-7 for providing compartments for storing flexible elongated members, such as wires or catheters.

FIG. 9 illustrates an exploded side view of the system 800 shown in FIG. 8. Similar to the interior component 400 and the exterior component 402 shown in FIG. 4, the system 800 includes an interior component 900 and an exterior component 902. The interior component 900 includes a surface 904 that can attach to an interior surface (not shown) of the exterior component 902 for forming interior passageways and pathways 810, 812, 814, and 816. The components 900 and 902 may be attached together by mating snap lock features 906 formed on the components 900 and 902.

It is noted that although FIG. 9 shows only two components for forming interior passageways, openings, and pathways, it should be understood that one or more additional components can be fitted within components 900 and 902 for forming additional interior passageways, openings, and pathways.

FIG. 10 illustrates a cross-sectional side view of the system 800 shown in FIG. 8. Referring to FIG. 10, the shows the components 900 and 902 in assembled together to form the system 800. The figure also shows that pathways 812 and 814 are formed between the components 900 and 902. Further, a side wall 1000 is formed by assembling the components 900 and 902 as shown.

In accordance with embodiments of the present disclosure, the storage systems disclosed herein may be made of any suitable material. For example, the components 900 and 902 shown in FIG. 9 may be made of plastic, metal, ceramic, or the like. The components may be made by any suitable manufacturing process such as, but not limited to, an injection molding process, a die process, or the like.

Figure 11:
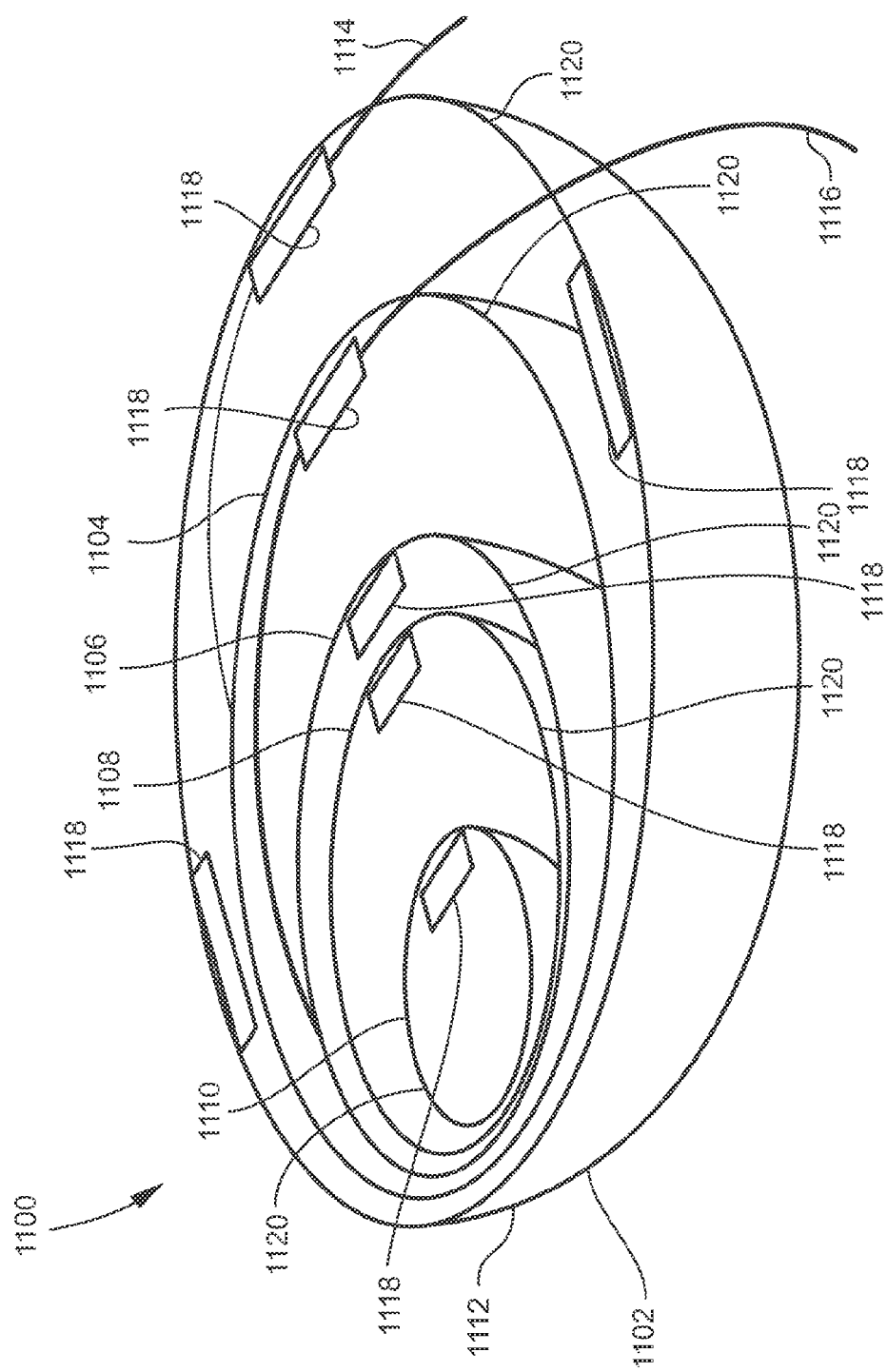
FIG. 11 is a top perspective view of another example storage system in accordance with embodiments of the present disclosure.

FIG. 11 illustrates a top perspective view of another example storage system 1100 in accordance with embodiments of the present disclosure. Referring to FIG. 11, the system 1100 includes multiple "bowl shaped" or "cup shaped" components 1102, 1104, 1106, 1108, and 1110 nested within one another as shown. Each component 1102, 1104, 1106, 1108, and 1110 is shown as being off-axis with one another; however, it is noted that the two or more of the components may share the same axis or otherwise suitably arranged with respect to each other. The components 1102, 1104, 1106, 1108, and 1110 may each be attached together at or near a point 1112.

During use of the system 1100, one or more wires, catheters, or other flexible elongated members may be stored for later retrieval. For example, FIG. 11 shows two wires 1114 and 1116 being stored in the system 1100 and with a respective end protruding for grasp by a person. The person may pull on the end to retrieve a wire from the system 1100. The portion of the wires 1114 and 1116 not shown may be coiled near a bottom of a respective component. For example, wire 1114 may be coiled within component 1102, and wire 1116 may be coiled within component 1104.

System 1100 may include multiple, respective protruding features 1118 that are each attached to and extend to an interior of a respective rim 1120. The features 1118 can be rigid or semi-rigid for holding wires within their respective component. For example, as shown in FIG. 11, portions of wires 1114 and 1116 are shown as being held underneath two of the features 1118.

Although the components of system 1100 are shown and described as being bowl or cup shaped, it should be understood that the components may alternatively be any other suitable shape and size. For example, the rims of the components may be oval in shape. In another example, the radius of the rims may be between about 2 inches and about 5 inches. In another example, the rim radius of the components 1102, 1104, 1106, 1108, and 1110 may be 5, 4, 3.5, 2.5, and 2 inches, respectively.

Figure 12:
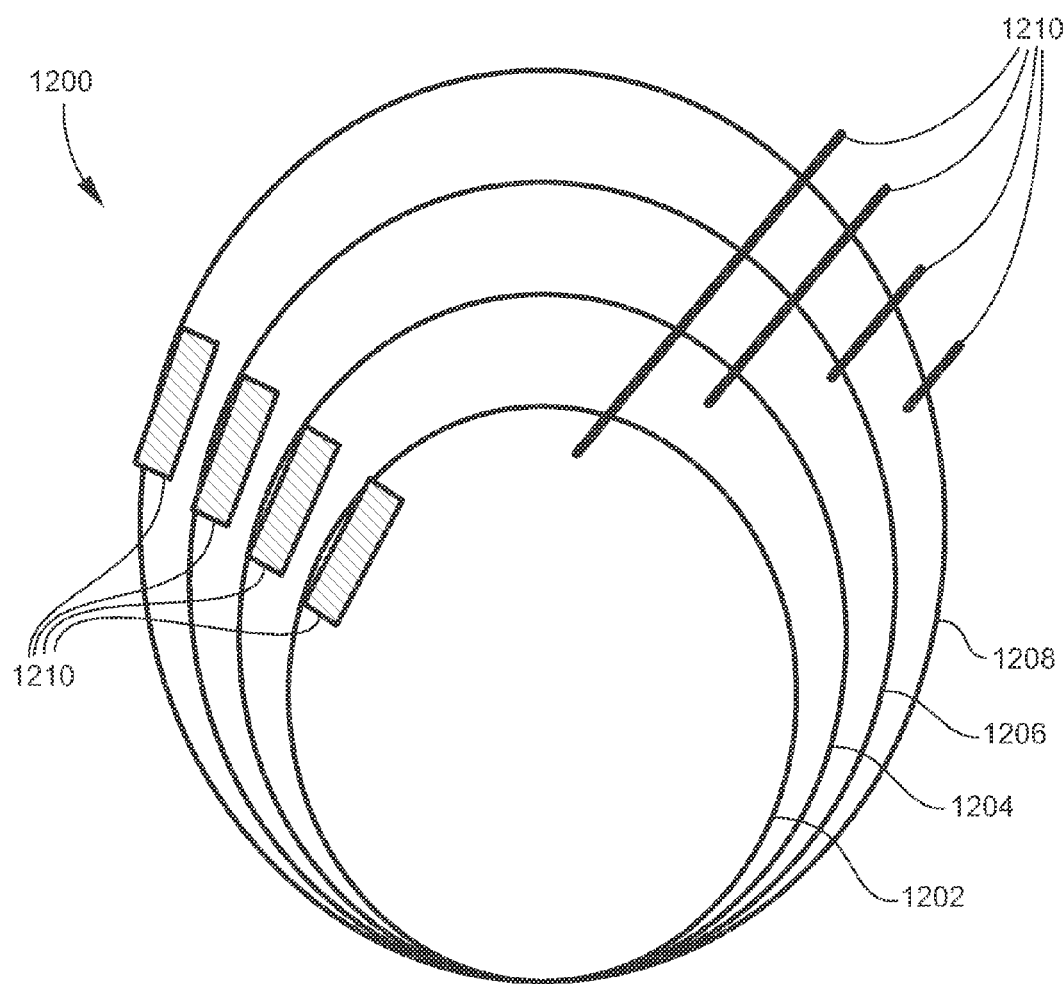
FIG. 12 is a top perspective view of another example storage system in accordance with embodiments of the present disclosure.

FIG. 12 illustrates a top perspective view of another example storage system 1200 in accordance with embodiments of the present disclosure. Referring to FIG. 12, the system 1200 is similar to system 1100 shown in FIG. 11. Particularly, the system 1200 includes multiple components 1202, 1204, 1206, and 1208 similar to the components of system 1100. Further, the system 1200 includes protruding features 1210 similar to the features 1118 shown in FIG. 11.

The system 1200 shown in FIG. 12 also includes tubes 1212 attached to the rims of the components 1202, 1204, 1206, and 1208 as shown for use in directing wires, catheters, or other flexible elongated members into a respective component. For example, an end of a wire may be fed through one of the tubes 1212 and the remainder may be coiled within a respective component. In this way, the wire end may be held in place by the tube 1212 for later retrieval. It is noted that the tubes 1212 can be made of any suitable material such as, but not limited to, plastic, rubber, and the like.

It is noted that the example systems described herein have a specific number of openings, pathways, and passageways. However, it should be understood that that systems can alternatively be configured to include any number of openings, pathways, and passageways in a similar configuration depending on the number of catheters and/or wires needed for a particular procedure.

It is noted that the openings, pathways, and passageways shown in the examples provided herein have generally square or rectangular cross-sectional shapes. However, it should be understood that the openings, pathways, and passageways may alternatively be formed of any other suitable shape. For example, they may be substantially circular, oval, or triangular.

Further, it is noted that the example passageways are generally circular in shape. However, it should be understood that the passageways may alternatively be shaped to run in any direction and may have an end such that they are not continuous as shown in examples described and shown herein.

The storage systems disclosed herein may have features of any suitable size and shape. For example, the storage system may be "bowl shaped" as shown in examples disclosed herein. A "bowl shaped" system may be a 8, 16, 32, 48, or 80 oz. container with dimensions between 3 and 15 inches. The height of a storage system may be, for example, between 1 and 4 inches. The openings, pathways, and passageways may have any suitable size. For example, the cross-sectional diameter may be between about 0.01 inches and about 0.3 inches.

In accordance with embodiments of the present disclosure, openings may be suitably attached to a tunnel or tube for guiding a wire or catheter from storage in a system. The tunnel or tube may be made of a suitable material such as, but not limited to, plastic, rubber, vinyl, latex, nylon, and the like.

In examples described herein, the openings are placed near the top portion of the side wall. However, it is noted that the openings may be suitably placed anywhere along the side wall. In an example, an opening is at least 0.5 centimeters from the bottom wall. The openings may be positioned high enough such that saline solution does not leak. In embodiments, an opening may be provided to allow for seepage of saline solution. For example, in such embodiments, saline solution may be poured into the interior space and the solution may seep through the opening to fill passageways and pathways.

Guide wires and catheters are often stored in saline solution or other storage fluid, such as a heparin, to maintain lubrication and prevent blood from clotting on the wire or catheter. As such, the storage systems disclosed herein may be used to hold the wire or catheter partially or substantially immersed in the storage fluid when storage fluid is placed in the system. In some embodiments, less than 1 centimeter of storage fluid is needed to keep the wires or catheters hydrated.

Storage systems in accordance with the present disclosure may have any suitable size and shape. For example, side walls may have an inner portion defining a variety of shapes, including, but not limited to, vertical, curved, or tapered interior surfaces of the side walls. Storage systems may have, for example, a diameter of 8 inches or less.

One skilled in the art will readily appreciate that the present subject matter is well adapted to carry out the objects and obtain the ends and advantages mentioned, as well as those inherent therein. The present examples along with the methods described herein are presently representative of various embodiments, are exemplary, and are not intended as limitations on the scope of the present subject matter. Changes therein and other uses will occur to those skilled in the art which are encompassed within the spirit of the present subject matter as defined by the scope of the claims.

What is claimed is:

1. A storage system comprising:
    a bottom wall; and
    a side wall including an upper end and an opposing lower end attached to the bottom wall, wherein the side wall defines a plurality of interior passageways between the upper and lower ends, wherein each interior passageway defines a loop shape that begins and ends at the same point in the interior passageway, wherein the side wall defines a plurality of openings at the upper end, and wherein each opening extends to a respective one of the interior passageways for storage of elongated flexible members, and wherein each opening defines a tapered pathway between an exterior of the side wall and the respective interior passageway.

2. The storage system of claim 1, wherein the bottom wall and the side wall form a bowl shape.

3. The storage system of claim 1, wherein the side wall is a continuous side wall that substantially surrounds the bottom wall.

4. The storage system of claim 3, wherein the side wall and the bottom wall are sealably attached together.

5. The storage system of claim 1, wherein each of the interior passageways are curved.

6. The storage system of claim 1, wherein the interior passageways are each positioned at different distances between the upper end and the lower end.

7. The storage system of claim 1, wherein the pathway of each opening tapers in a direction from an end connecting to the respective interior passageway to an opposing end.

8. The storage system of claim 1, wherein each opening is positioned at a different location along the upper end of the side wall.

9. The storage system of claim 8, wherein the bottom wall and the side wall comprise first and second components having surfaces that are attached together to form the interior passageways.

10. The storage system of claim 1, wherein the bottom wall and the side wall are made of one of plastic, metal, and ceramic.

11. The storage system of claim 1, wherein the interior passageways have a cross-sectional diameter between about 0.01 inches and about 0.3 inches.

12. The storage system of claim 1, further comprising a structure attached to the bottom wall and extending within an interior space defined by the side wall.

13. The storage system of claim 12, wherein the structure is conical in shape.

14. The storage system of claim 12, wherein the structure is centered within the interior space.

\* \* \* \* \*